United States Patent [19]

Jungnelius

[11] Patent Number: 5,735,828
[45] Date of Patent: Apr. 7, 1998

[54] METHOD AND DEVICE FOR CATHETERIZATION

[76] Inventor: Bjorn Erik Jungnelius, Licknatte, Stenkyrka, S-620 33 Tingstade, Sweden

[21] Appl. No.: 537,906

[22] PCT Filed: Apr. 26, 1994

[86] PCT No.: PCT/SE94/00374

§ 371 Date: Feb. 5, 1996

§ 102(e) Date: Feb. 5, 1996

[87] PCT Pub. No.: WO94/25096

PCT Pub. Date: Nov. 10, 1994

[30] Foreign Application Priority Data

Apr. 26, 1993 [SE] Sweden ................... 9301392

[51] Int. Cl.⁶ ................................................. A61M 5/00
[52] U.S. Cl. ................................. 604/264; 604/20
[58] Field of Search ................................. 604/282, 280, 604/264, 51, 52, 53, 20, 21, 22, 28

[56] References Cited

U.S. PATENT DOCUMENTS

| | | | |
|---|---|---|---|
| 3,472,232 | 10/1969 | Earl | 604/280 |
| 3,827,434 | 8/1974 | Thompson et al. | 604/280 |
| 3,853,130 | 12/1974 | Sheridan . | |
| 4,354,491 | 10/1982 | Marbry | 604/280 |
| 4,619,644 | 10/1986 | Scott . | |

FOREIGN PATENT DOCUMENTS

| | | |
|---|---|---|
| 0 067 260 A1 | 12/1982 | European Pat. Off. . |
| 0 545 671 A1 | 6/1993 | European Pat. Off. . |
| WO82/03558 | 10/1982 | WIPO . |

*Primary Examiner*—John D. Yasko
*Attorney, Agent, or Firm*—Pollock, Vande Sande & Priddy

[57] ABSTRACT

A device for cardio-vascular catheterization constituted by a tubular member with a tip and an unbroken head permanently connected to the member. A channel extends through the entire length of the device, and a slit extends from the tip toward the head, forming a channel along the extension of the slit.

10 Claims, 4 Drawing Sheets

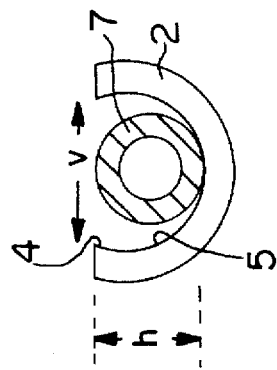
FIG. 6
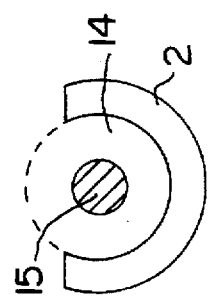
FIG. 7
FIG. 8
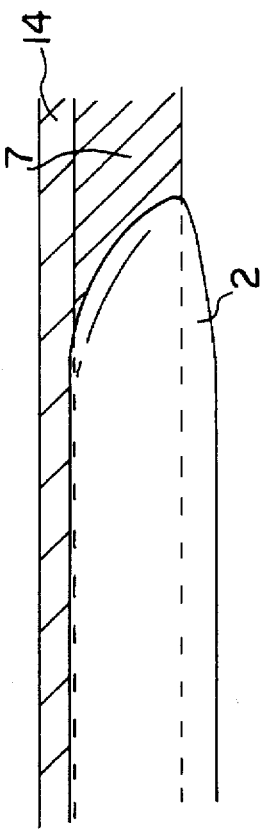
FIG. 9
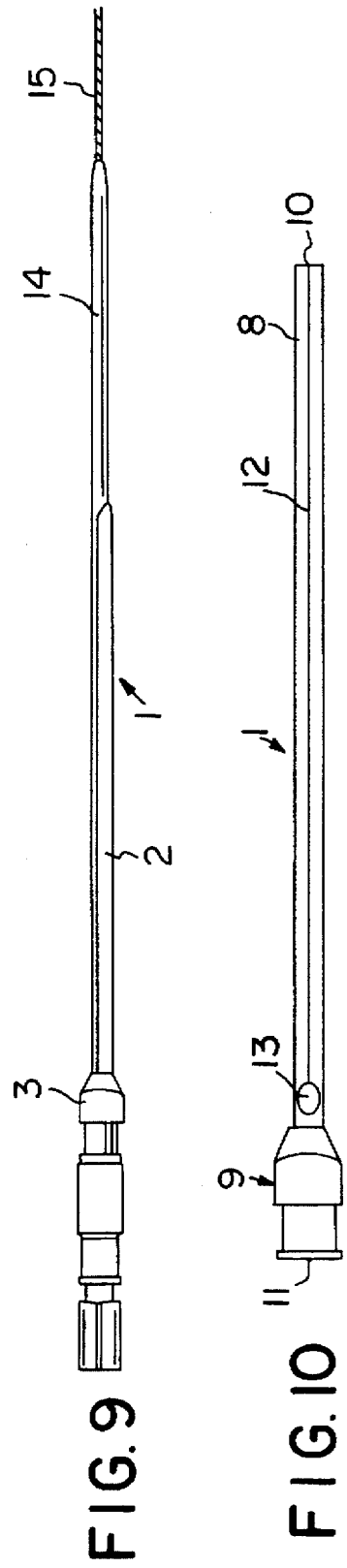
FIG. 10

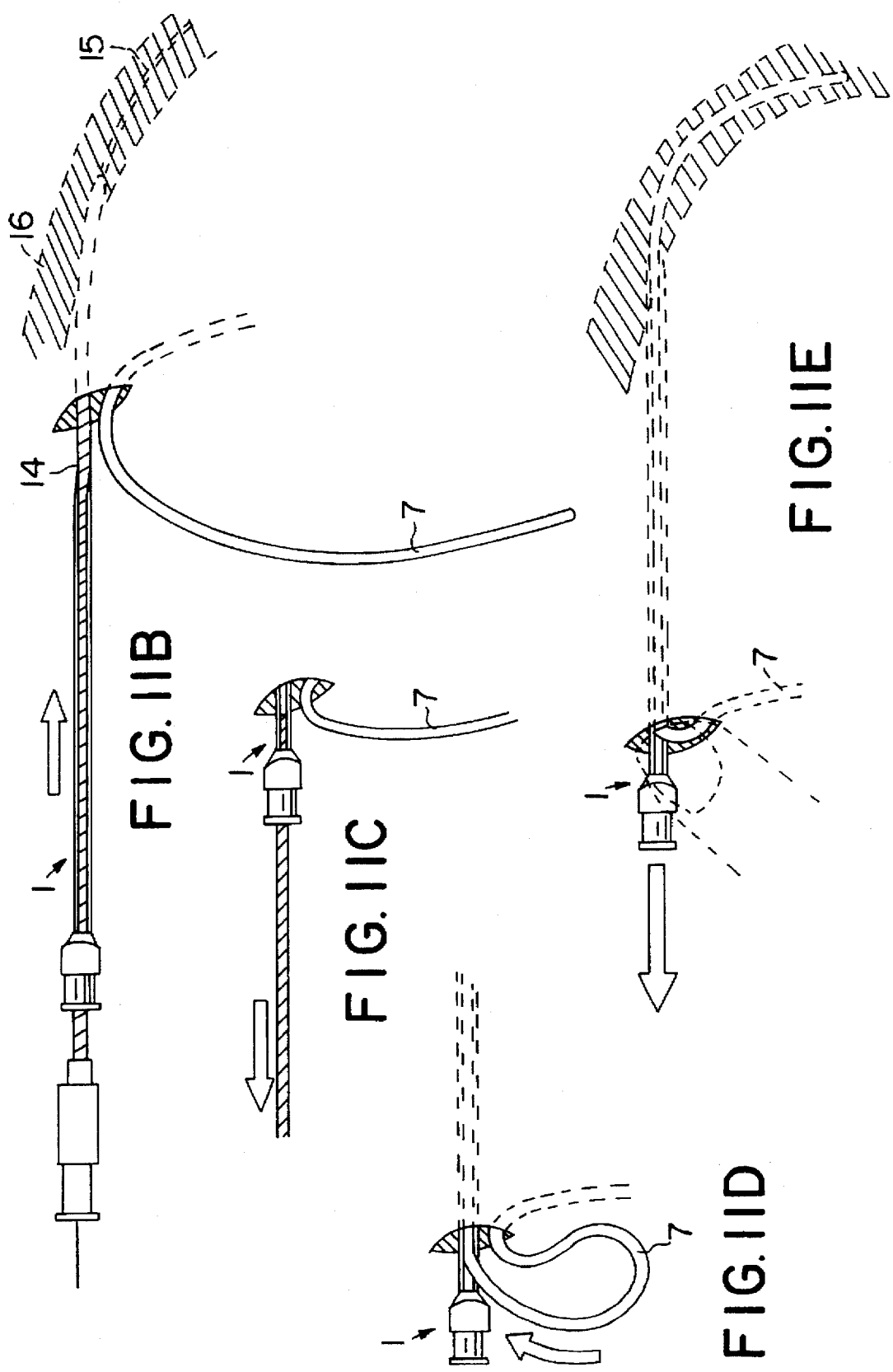

METHOD AND DEVICE FOR CATHETERIZATION

FIELD OF THE INVENTION

The present invention refers to a process for catheterization of the vascular system and a device for carrying out this process.

BACKGROUND OF THE INVENTION

A previously known device for guiding a catheter into its position in a blood vessel is disclosed in SE-A-404 491. The device consists of a head part and a sheath with a slit along the entire length of the device, both tubular and head member included. The sheath is made of a flexible material with the slit extending along its entire extension. Similar devices are known from U.S. Pat. No. 3,853,130, EP-A-00911434, U.S. Pat. No. 3,472,232, U.S. Pat. No. 4,619,644 and EP-A-0067260.

These prior art devices have the following disadvantages:

U.S. Pat. No. 3,472,232 consists of several movable parts and has no wide slot, making a deformation of the catheter unavoidable. EP-A-0067260 requires a deformation to create or enlarge a slit (with a resulting increase in the outer diameter of the device). U.S. Pat. No. 4,619,644 is not designed for flexible long catheters without stiffening guide-wires that must subsequently be extracted. Neither U.S. Pat. No. 3,472,232 nor U.S. Pat. No. 4,619,644 are designed for use with the Seldinger technique, the most atraumatic and safe method.

Catheters are introduced into the vascular system to create a link to the outside world. If great and fast dilution exists, the administration of highly irritating solutions will be possible. For this reason central vessels close to the heart are catheterized when delivering cytotoxics, certain antibiotics and amino acids.

A centrally positioned catheter can be connected to a port, subcutaneously placed by surgery, and a system concealed from the outside world will be obtained. When necessary, this system can be connected to the outside world by penetrating the silicone top of the port (and the skin) with a special cannula, which in turn is connected to an infusion system.

Catheters inserted in "central" veins are soft and highly flexible, in size and consistency like boiled spaghetti. In order to penetrate the skin and underlying tissues as well as the wall of a vessel, a tube or sheath through which the catheter will be introduced or, alternatively, a guide-wire over which the catheter will be advanced into the vascular lumen, is required. The intravascularly positioned catheter is connected to infusion systems via standardized attachments or connected to a subcutaneously placed port. Catheters are often tunnelled in order to minimize the risk of infection or simply for practical reasons, giving the port or catheter a convenient position.

1. Direct Method

The direct method implies introduction of the catheter through a sufficiently large cannula after positioning of the latter in the vascular lumen. This method postulates a large cannula (inner-diameter=catheter diameter), and a "stripped" catheter without mounts, attachments or port.

2. Indirect Method

A cannula with an enveloping plastic sheath on the outside is introduced into the vascular lumen, the sheath is passed over the cannula into a vessel and the cannula is thereafter extracted. The catheter is inserted through the sheath. This method requires a "stripped" catheter and a rather large cannula.

3. Seldinger Technique

Method A:

A guide-wire is inserted through a small bore cannula into the lumen. A catheter is threaded over the guide-wire reaching an intraluminar position.

Disadvantage: The guide-wire may not make sharp turns as the friction between catheter and guide-wire at the insertion of the catheter, or extraction of the guide-wire, will be too great and the catheter will get caught. The guide-wire is extracted through the distal end of the catheter, making a port impracticable.

Method B:

A guide-wire is introduced into the vascular lumen via a small bore cannula. A plastic sheath with a tapered proximal end and a plastic tubular sleeve on the outside is pushed or forced into the vessel, and the tubular sleeve pushed in, whereupon the sheath (dilator) and guide-wire is extracted. The catheter is inserted through the remaining tubular sleeve into the tureen and the sleeve is pulled out. The Seldinger technique allows a small bore cannula (atraumatic). The disadvantage of this method is that it requires a "stripped" catheter. The method postulates tunnelling as a last step.

The problems with the methods described above are:

The sheath or sleeve has to be extracted over a "stripped" catheter by being drawn over the distal end, for which reason no port or attachment can be connected to it until later. The connection will then take place under sub-optimal conditions.

When a guide-wire is used, it has to be extracted through the distal end of the catheter to which no port can be connected. A catheter advanced over a guide-wire will, because of friction, easily stick to the guide-wire in sharp turns and is often caught by surrounding tissues when penetrating narrow passages on the way between skin and vessel. When extracting the guide-wire from the inserted catheter, the risk of getting caught is even greater, and sharp bends may make extraction impossible.

Tunnelling is always required as a last step when using any of the methods described above.

SUMMARY OF THE INVENTION

It is, accordingly, an object of the present invention to provide a technique for catheterization, preferably of the central vascular system, and the provision of an insertion device with which this technique becomes possible, eliminating the problems with the prior art methods described above, not postulating rigid catheters for removal of the device as a condition with this catheterization technique, the minimal friction between sheath and catheter preventing the latter from slipping out.

An additional object is to minimize the space needed between the catheter coming out of the subcutaneous runnel and the puncture size of the insertion device, a roughly 5–10 mm long incision with underlying subcutaneous pocket without restriction in depth.

A further object is to eliminate the risk of kinking when using a flexible catheter.

Owing to the technique and the device according to the present invention, the problems described above are avoided by the use of an "open" sheath, metal or plastic, with an unbroken head at the distal end. The catheter is inserted in front of the head member through an opening that is insignificantly larger than the diameter of the catheter. The sheath may, proximal to the opening, be provided with a slot identical in width to the opening. In this case, the opening forms the beginning of the slot, i.e., it has a head part and a tubular part provided with a long slot. Alternatively, the sheath may be furnished with a slit proximal to the opening. In this case, the sheath is conveniently made of a thin plastic material.

Existing devices make it necessary for the catheter to be inserted through the head member of the sheath, leaving a catheter-loop of several centimeters which, after the extraction, will kink if a flexible catheter is used. In the slot of the device according to the present invention, the catheter can be inserted as proximally as possible, as the width of the slot exceeds that of the catheter. Insertion of central venous catheters, with or without the use of subcutaneous tunnelling or insertion of subcutaneous ports, is exclusively made with "closed" devices generally utilizing the Seldinger technique.

Simple removal of the sheath from the catheter and simple construction of the sheath, making it economical to manufacture, has thus far been an obstacle to the widespread use of "open" sheaths. The device according to the present invention meets those requirements by providing an unbroken head member and an opening proximal to it. Being adapted to the Seldinger technique, the method requires only moderate alteration of present techniques, notwithstanding considerable simplification.

In present kits for introduction of central venous catheters or implantation of ports, only one sort of sheath need be changed for another in order to obtain a substantial improvement of the catheterization technique.

An object of the invention is the provision of a technique and a device for catheterization of preferably central veins. When using long, flexible unstiffened catheters for catheterization of central veins, it is an advantage to be able to make all necessary connections to attachments or ports in advance, and to accomplish tunnelling prior to the introduction of the catheter into the vein. This requires an "open" device not extracted over the distal end of the catheter. The device according to the present invention solves this problem by having an open sheath with an open duct or groove forming a slot in front of an unbroken head member. By introducing the catheter proximally to the head, a strong head-end is obtained and the groove may therefore be made wider than the catheter. When extracting the sheath, the insignificant friction between the catheter and slot permits the use of very flexible catheters possible. The same applies to the alternative thin sheath with an opening and a slit.

The simplicity and function of the design, distinguishing it from the other existing "open" devices, makes it possible to replace the present dominant "closed" techniques with the "open" technique without increase in complexity or higher costs.

BRIEF DESCRIPTION OF THE DRAWINGS

The present invention will now be described in more detail by reference to the drawings, which show several embodiments thereof.

FIG. 6 is a sectional top view of the proximal part of tubular member of the device, schematically showing the positions of the catheter and dilator;

FIG. 7 is a cross-section on the line VII—VII in FIG. 4, showing the dilator and guide-wire in proper positions;

FIG. 8 is a sectional view of FIG. 7 showing the catheter in the proper position;

FIG. 9 is a side elevation of the device with dilator and guide-wire;

FIG. 10 is a top view of a second embodiment of the device of the present invention; and FIGS. 11a to 11f show partly sectional views illustrating the process of using the device of the present invention for catheterization.

DESCRIPTION OF PREFERRED EMBODIMENT

Figure 1:
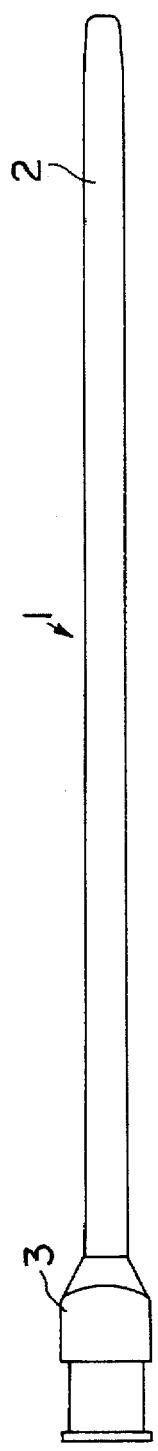
FIG. 1 is a bottom view of a first embodiment of the device according to the invention.
Figure 2:
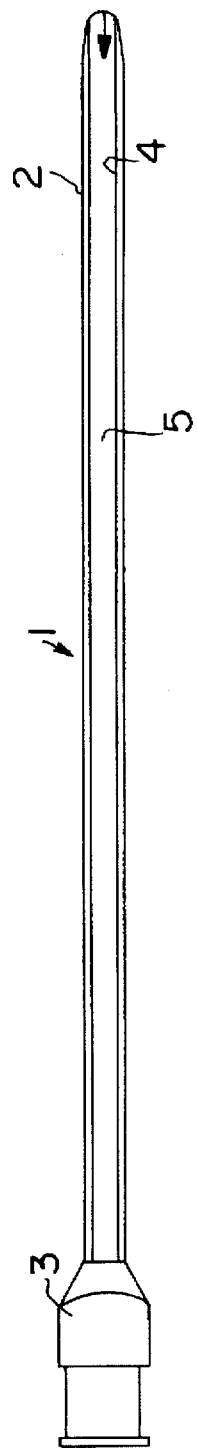
FIG. 2 is a top view of the device.
Figure 3:
FIG. 3 is a side elevation of the device.
Figure 4:
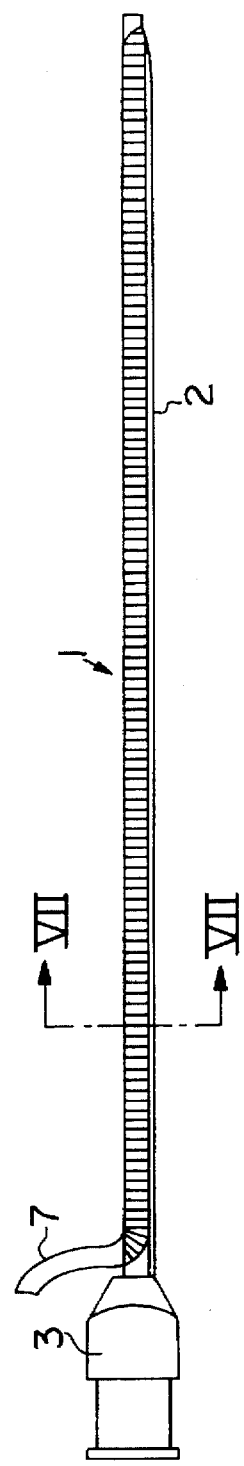
FIG. 4 is a sectional side view of the device, showing the catheter having entered the slot.
Figure 5:
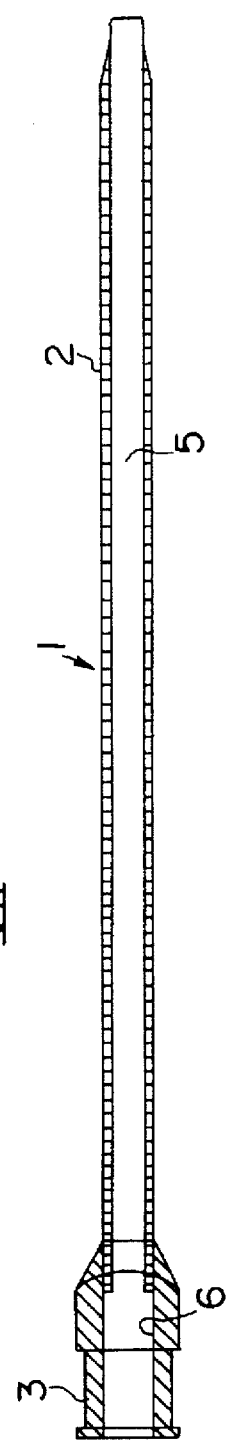
FIG. 5 is a sectional top view of the device.
Figure 11F:
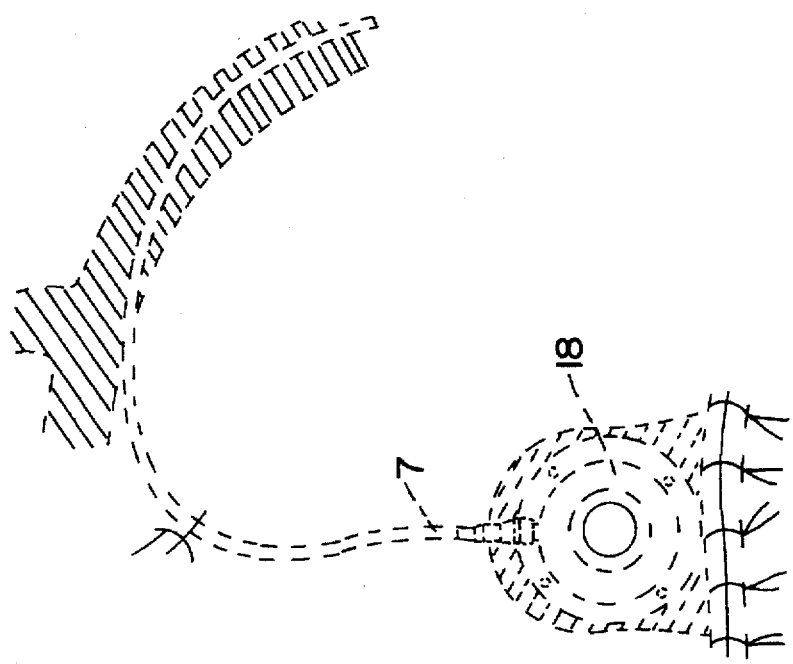
Figure 11A:
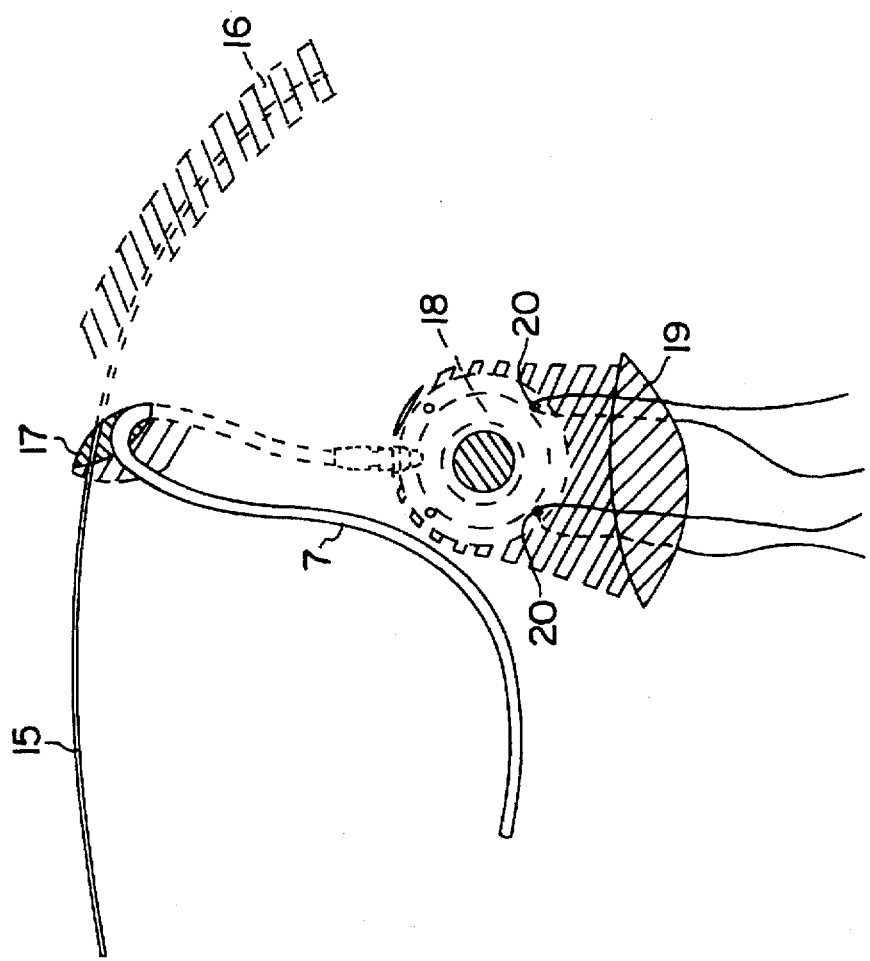

FIGS. 1 to 9 show the device 1 of the present invention, consisting of a tubular member 2 and a head member 3. The sheath is provided with a slot 4 extending from the distal end of the sheath toward the head, so that a groove or channel 5 is produced, defined by the inner wall of the sheath and open via the slot and forward, also connected to the central opening 6 of the head (FIG. 5). FIG. 4 shows how a catheter 7 is positioned in the sheath when accomplishing the technique according to the present invention. The catheter 7 is not inserted through the opening of the head-member, for reasons explained below.

FIG. 10 shows an alternative embodiment of the device 1 of the present invention, also consisting of a tubular member 8 and a head member 9 having an opening (not shown) extending all along the device through both ends 10 and 11. At least the tubular member 8 is made of a thin and flexible material having a narrow slit 12 extending from the proximal end 10 towards the head 9 and terminating in a wide opening 13.

FIGS. 6 to 8 show the correct positions of the sheath 2, catheter 7, a dilator 14 and guide-wire 15, in the first embodiment of the invention during different steps of the process.

As seen in the drawings, the slot preferably has a width smaller than the inner diameter of the sheath (FIG. 7) in order for its edges to grip around the dilator, keeping it firmly within the sheath. Later, when the catheter is guided through the sheath, a "roof" is formed between these edges by the surrounding tissues, preventing the catheter from escaping out of the sheath, so that, when advanced, it will be guided into the vessel.

The process of catheterization in accordance with the present invention will now be described with reference to FIGS. 11a to 11f. A central vein 16 is located with a syringe when administrating local anaesthetics. A small bore cannula is inserted into the vascular lumen on the basis of the previously located position, whereupon the guide-wire 15 is advanced to the vessel 16 through the cannula to a radiographically verified position in the superior caval vein.

After removal of the cannula, a small incision is made in the skin and an underlying subcutaneous "pocket" 17 is formed. The catheter 7 and the port 18 are now connected if that has not been done at an earlier stage. The catheter 7 is cut to the proper length according to the radiographic information. A skin incision with a length slightly greater than the diameter of the port is made just distal to the intended position of the port 18. By blunt dissection, a subcutaneous pocket 19 just wide enough to accept the port and long enough to permit the latter to be pushed in completely is formed.

The catheter 7 is tunnelled through the pocket to the place of the guide-wire 15 where the previously made 1 cm long pocket is located. Thus the catheter 7 and guide-wire 15 emerge into and out of the same opening. During this tunnelling maneuver, the port 18 will be placed in its pocket 19 so that it barely disappears from sight. Two ligatures 20 are put in fascia in the bottom of the distal end of the pocket and threaded through the posterior holes of the port just before it is pushed in.

The device according to the present invention, with dilator 14 included, is then passed over the guide-wire 15 into the vessel 16, and pushed in, whereupon the dilator is removed.

The catheter 7, with its length corrected earlier, is then inserted through the slot-opening of the tubular member 2 and guided on as far as possible. At this point, only a minimal portion of the catheter, possibly kinked, is visible in the subcutaneous pocket at the puncture site. The device is now extracted, the catheter 7 being held in place with slight finger pressure.

In order to minimize the risk of bleeding or aspiration of air, the dilator 14 is removed just prior to the insertion of the catheter 7 into the tubular member. It is understood that the patient is positioned in such a way that a verified positive central venous pressure exists.

The ligatures 20 attaching the distal part of the port 18 to the surrounding tissues are tied, pulling it backwards somewhat so that the catheter is tightened slightly and any eventual kink at the site of the proximal incision is stretched out. If the port does not move backward, any possible kinked loop will disappear after "massage". Finally the dermis and possible the subcutis are sutured.

If a plastic sheath of a thinner material is being used, the slit 12 with which it is provided will open by itself when the sheath is extracted, provided that the catheter is held by a finger at the moment of extraction, preventing it from accompanying the sheath out.

As an alternative to the use of a dilator, the device according to the invention can be placed on the outside of a relatively large-bore cannula, which is introduced directly into the vessel, whereupon the sheath is pushed in. The diameter of the cannula will then be equal to the inner diameter of the tubular member and somewhat larger than that of the catheter.

With the use of the device of the present invention, all necessary connections can be made by the manufacturer under optimum conditions. The length of the catheter can readily be corrected during the operation by cutting off the proximal part of the catheter, or simply by using a few prefabricated standard lengths.

The technique according to the present invention achieves simplification, increased safety and faster execution, especially if subcutaneous tunnelling and implantation of port systems are made.

The device according to the present invention has a standardized head 3 at the distal end to which syringes or standardized attachments can be connected. Being "unbroken", it has maximum stability and even violent connections cause no alteration to its shape.

Consequently, the head constitutes a firm foundation of the tubular member, so that, despite the opening, the slot or slit has an acceptable rigidity in the head end. This allows a width of the tubular opening and slot almost equal to the inner diameter of the sheath. Thus it permits lateral introduction of a catheter, with a diameter almost equal to the diameter of the tubular inner lumen.

The slot 5 has a width insignificantly exceeding the diameter of the catheter 7, making extraction of the catheter possible with minimal effort. As the catheter is inserted through the tubular member, the surrounding tissues form a defined roof, preventing the catheter from escaping out through it.

The device may have an inner tubular diameter of 2 mm, and a length of 85 mm. The outer tubular diameter of the tubular member may be 2.6–3 mm, depending on the material, and the outer diameter of the catheter is preferably 1.6–1.8 mm.

When the sheath is being extracted, the flexible catheter must not accompany it at all, not even by a fraction of a centimeter, as this would result in a loop with the risk of kinking at the puncture site. The "unbroken" head and the slot constitutes a sheath with no movable parts, sufficient stability of form and a simple design, making it simple to manufacture.

The device is designed to be used with a dilator 14, having an outer diameter equal to the inner diameter of the tubular member. The bevelled end of the dilator starts approximately 5 mm distal to the end of the tubular member. The end of the tubular member 10 is bevelled and forms a smooth transition between itself and the dilator 14 in order not to get caught in the wall of the vessel when the latter is penetrated.

The device according to the invention can be manufactured of either steel or plastic material so dimensioned that no or insignificant flexure exists. If the material is too thin, the sheath 2 will be flexible to a degree at which the slot enlarges when bent or the tubular member gets squeezed by the surrounding tissues as the dilator is extracted.

The outer diameter of the dilator is preferably slightly less than the inner diameter of the tubular member in order to fit exactly inside the latter. The length of the dilator and cannula should preferably exceed that of the sheath by at least 50 and 15 mm, respectively, and the guide-wire should have a length that exceeds the sheath by at least 150 mm. The dimension of the soft catheter in relation to the device are: an outer diameter less than the width v of the slot and less than the height h of the channel, 75–80% of the inner lumen diameter being the optimum.

The second embodiment of the device according to the invention replaces the wide slot described above with a narrow slit 12 in front of the opening 13 (FIG. 10). The thin material of the tubular member makes its extraction possible as the slit easily opens itself to the catheter. The slit makes the tubular member more stable than a slot. Notwithstanding the pressure of the surrounding tissue, the inner lumen remains intact.

What is claimed is:

1. A device for the catheterization of a cardio-vascular system, comprising a longitudinally extending tubular member made of a thin and flexible material, said tubular member having a tip end and a distal end, a head member permanently connected to said distal end, a catheter receiving channel extending along an extension of said tubular member and said head member, and a narrow slit extending along said tubular member toward said head member, wherein said slit terminates in an opening proximal to said head member and having a width insignificantly larger than a diameter of a catheter to be received in said channel.

2. A device according to claim 1, wherein said opening extends toward said tip end.

3. A device according to claim 1, wherein said slit (4) extends along the entire length of the tubular member and has a width corresponding to approximately 60 to 90% of the diameter of an inner lumen of said tubular member.

4. A device according to claim 1, wherein said slit has a width less than the inner diameter of the tubular member.

5. A device according to claim 1, wherein the tip of said tubular member (2) is bevelled to form a smooth transition to a dilator placed therein.

6. A device according to claim 1, wherein the tubular member (2,8) has an oblong opening (13) in front of the head member having a width less than the inner diameter of the lumen of said member, but exceeding the outer diameter of the catheter(7), and a slit (12) having a straight extension from said opening (13) to said tip.

7. A device according to claim 1, wherein the tubular member (2,8) is made of a thin plastic material dimensioned so that the catheter can be extracted through the slit with a minimum of resistance and that the tubular member bends over an intravascularly curved dilator, edges of the tip being bevelled to avoid interference with the surrounding tissue.

8. A method for catherization of a central venous system, said method comprising the steps of:
   (a) introducing into a vessel a flexible oblong part, preferably consisting of a dilator and guide-wire;
   (b) threading a sheath provided with a slit onto said part and guiding said sheath into said vessel;
   (c) extracting said oblong part from said vessel and said sheath;
   (d) introducing a catheter directly into the slit of said sheath and guiding said catheter into said vessel; and
   (e) extracting said sheath.

9. The method of claim 8, wherein the vessel is located with a cannula through which the guide-wire is passed and the location is verified radiographically.

10. The method of claim 8, including passing a dilator over said guide-wire and said sheath over the dilator, which is extracted when a proximal end of the sheath is in an intraluminar position, so that the soft catheter, which previously preferably has been tunnelled subcutaneously, can be introduced proximal to the head member, through the slit to the lumen of the vessel, whereupon said sheath is extracted, allowing said catheter to escape through said slit.

* * * * *